United States Patent
Yamazaki et al.

(10) Patent No.: US 10,434,436 B2
(45) Date of Patent: Oct. 8, 2019

(54) GAS-BLOWING VAPORIZING AND DRYING DEVICE

(71) Applicants: Tomoyuki Yamazaki, Kyoto (JP); Przemyslaw Stasica, Hertfordshire (GB); Bob Boughtflower, Hertfordshire (GB)

(72) Inventors: Tomoyuki Yamazaki, Kyoto (JP); Przemyslaw Stasica, Hertfordshire (GB); Bob Boughtflower, Hertfordshire (GB)

(73) Assignee: Shimadzu Co., Kyoto (JP)

( * ) Notice: Subject to any disclaimer, the term of this patent is extended or adjusted under 35 U.S.C. 154(b) by 780 days.

(21) Appl. No.: 13/972,036

(22) Filed: Aug. 21, 2013

(65) Prior Publication Data

US 2014/0053988 A1 Feb. 27, 2014

(30) Foreign Application Priority Data

Aug. 22, 2012 (JP) ................................ 2012-183561

(51) Int. Cl.
- *B01L 3/00* (2006.01)
- *B01D 1/18* (2006.01)
- *G01N 1/40* (2006.01)

(52) U.S. Cl.
CPC ............ *B01D 1/18* (2013.01); *B01L 3/50825* (2013.01); *B01L 2200/0678* (2013.01);
(Continued)

(58) Field of Classification Search
CPC ............... G01N 35/10; G01N 35/1009; G01N 35/1034; B01L 3/50825; B01L 2300/04; B01L 2300/046; B01L 2300/048
(Continued)

(56) References Cited

U.S. PATENT DOCUMENTS

| 5,169,602 | A | * | 12/1992 | Pang | .................... | A61J 1/20 |
| | | | | | | 215/247 |
| 5,945,070 | A | * | 8/1999 | Kath | .................... | B01J 19/0046 |
| | | | | | | 422/535 |
| 2012/0018100 | A1 | | 1/2012 | Iwata et al. | | |

FOREIGN PATENT DOCUMENTS

| CN | 102405407 A | 4/2012 |
| GB | 2465955 A | 6/2010 |

(Continued)

OTHER PUBLICATIONS

Examination Report Received for Chinese Patent Application No. 201310367574.8, dated Jan. 30, 2015, 10 pages (2 pages of English Translation and 8 pages of Official Copy).

(Continued)

*Primary Examiner* — Jill A Warden
*Assistant Examiner* — Dwayne K Handy
(74) *Attorney, Agent, or Firm* — Chris Mizumoto

(57) ABSTRACT

Provided is a gas-blowing vaporizing and drying device, which includes: a sample tube in the form of a double tube including an inner tube for a solution and an outer tube for a gas, the inner tube protruding from one end of the outer tube by length L; and a collection container including a container body and a lid provided with a protrusion sleeve tube, the protrusion sleeve tube including a coupling portion at an end to be located outside the container body and a sleeve portion of a length equal to or longer than L having an open end to be located inside the container body, the coupling portion being designed to be coupled to the aforementioned one end of the outer tube in an air-tight manner.

5 Claims, 6 Drawing Sheets

(52) U.S. Cl.
CPC ... *B01L 2300/044* (2013.01); *B01L 2300/048* (2013.01); *G01N 2001/4027* (2013.01)

(58) Field of Classification Search
USPC .................. 422/501, 509, 511, 512, 522
See application file for complete search history.

(56) References Cited

FOREIGN PATENT DOCUMENTS

| | | |
|---|---|---|
| JP | 2003-149217 A | 5/2003 |
| WO | WO-2009/044425 A1 | 4/2009 |
| WO | WO-2009/044426 A1 | 4/2009 |
| WO | WO-2009/044427 A1 | 4/2009 |
| WO | WO-2009/044428 A1 | 4/2009 |

OTHER PUBLICATIONS

United Kingdom Office Action dated Feb. 17, 2014 for the corresponding Application No. GB1315004.0 (6 pages).

\* cited by examiner

1mm

Fig. 6A
Fig. 6B
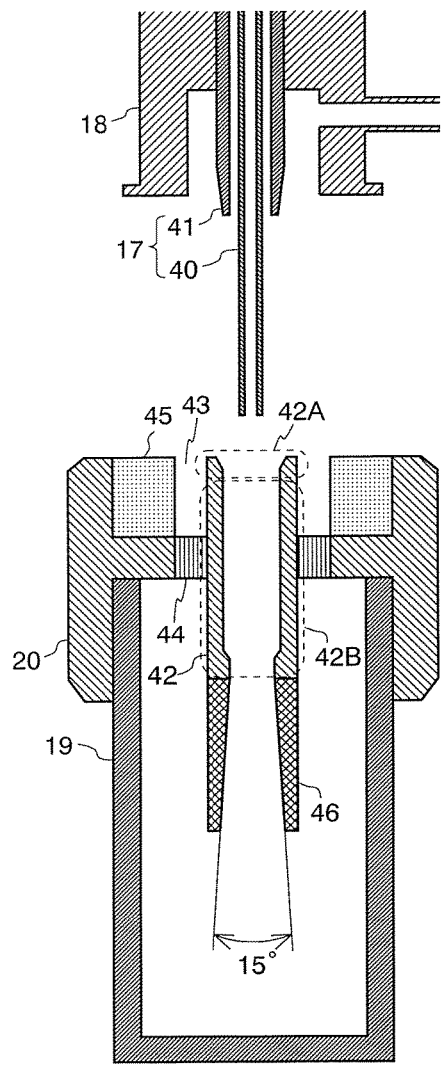
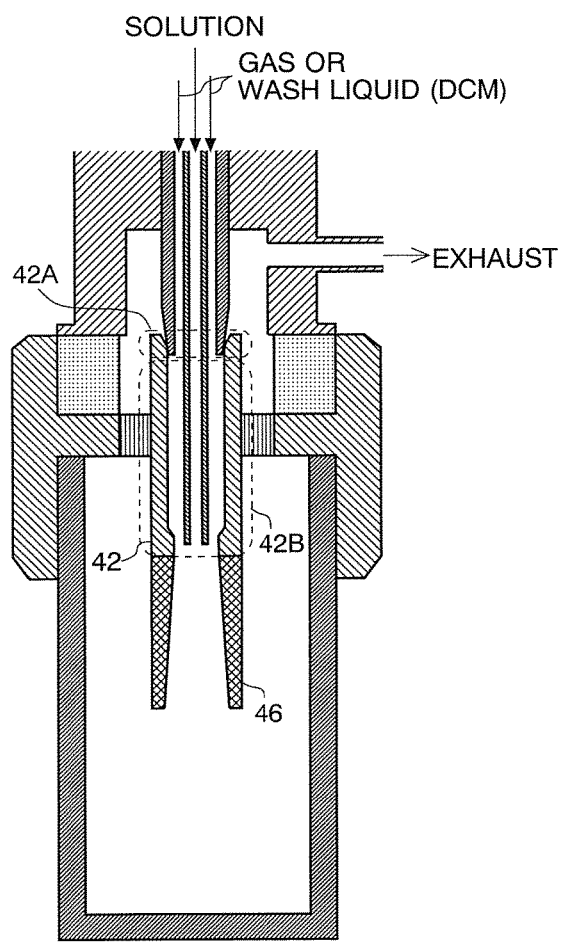
Fig. 7

GAS-BLOWING VAPORIZING AND DRYING DEVICE

TECHNICAL FIELD

The present invention relates to a gas-blowing vaporizing and drying device for nebulizing a solution containing a target component by blowing an amount of gas at the solution being dropped in a collection container and then drying the solvent to collect the target component in solid form (powder). The present gas-blowing vaporizing and drying device can be suitably used in a preparative separation-purification system for separating one or a plurality of components in a solution by using a liquid chromatograph and for purifying and collecting each component.

BACKGROUND ART

Preparative separation-purification systems using liquid chromatographs are used in pharmaceuticals or similar fields in order to collect samples to be stored in the form of a library. In a system disclosed in Patent Document 1, target components (compounds) in a sample solution are temporally separated by a liquid chromatograph. The separated target components are then introduced into respective trap columns and temporarily captured therein. Subsequently, a solvent is passed through each trap column to elute the captured component from the trap column and collect the solution containing the target component in a container. Then, the collected solution is subjected to a drying process to remove the solvent and collect the target components in solid forms.

The drying process is normally performed by heating the collected solution. This process must be performed at a moderate temperature since too high a temperature will change the quality of the target component. Accordingly, the processing time will be rather long, which may reach several hours or even up to one day for some components. This drying process consumes the longest period of time in the preparative separation-purification process. Therefore, it is essential to shorten this period.

A method for solving this problem is disclosed in Patent Documents 2-5, in which the solution is dropped in a collection container in which an amount of air, nitrogen or another kind of gas is supplied to nebulize the solution, thus promoting the vaporization of the solvent.

Figure 8A:
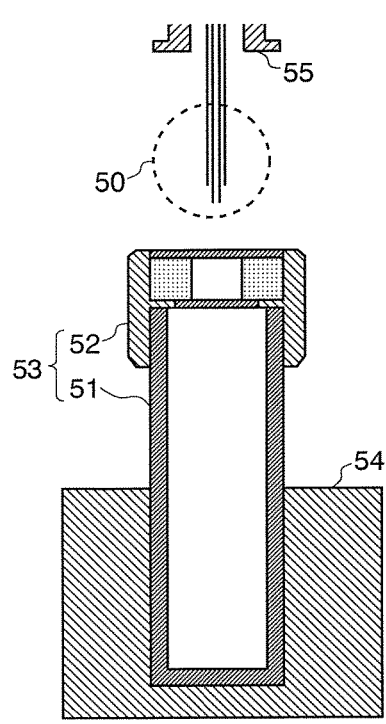
Figure 8B:
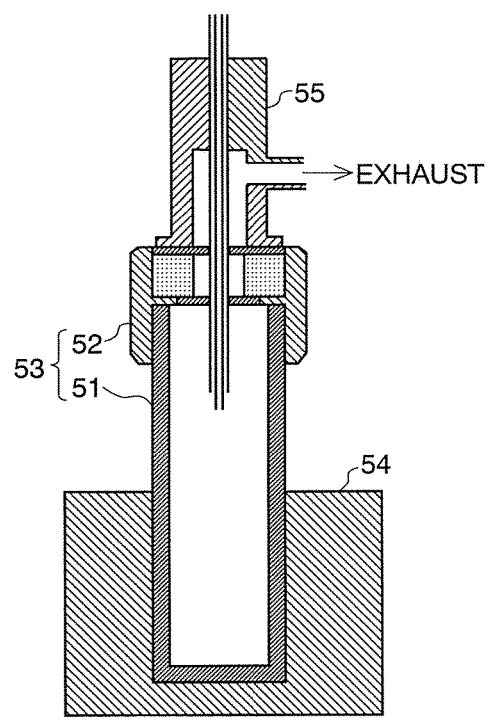
Figure 8C:
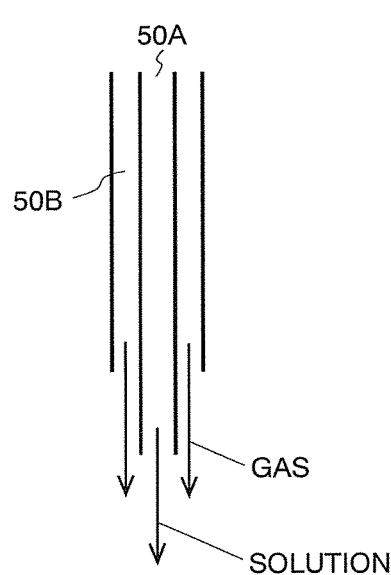
Figure 8D:
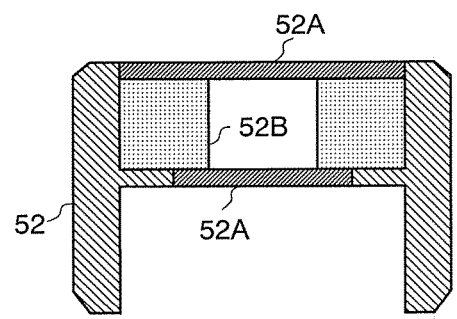

A normal procedure of the drying process according to the method of Patent Documents 2-5 (which is called the "gas-blowing vaporizing and drying process" in this specification) is hereinafter described by means of FIGS. 8A-8D. A preparative separation-purification system has a needle 50 having a double-tube structure which includes a solution-introducing tube 50A and a gas-introducing tube 50B which circumferentially covers the solution-introducing tube 50A, as shown in FIG. 8C. A collection container 53 held in a temperature regulation block 54 is placed below the needle 50. The collection container 53 has a container body 51 and a cap 52 which can be put on the upper opening of the container body 51. The cap 52 has two septa 52A and a doughnut-shaped cushion 52B sandwiched between the two septa 52A.

In this process, the needle 50 is lowered, penetrating the septum 50A and passing through the central hole of the cushion 52B, until its tip is inserted into the collection container 53. Along with this descending motion of the needle 50, an exhaust duct 55 is also moved downward and hermetically pressed on the cap 52 by an elastic force of the cushion 52B so as to cover the hole created in the cap 52 by the needle 50. Subsequently, a solution and a gas are respectively introduced through the solution-introducing tube 50A and the gas-introducing tube 50B into the collection container 53.

After passing through the solution-introducing tube 50A, the solution is dropped from the tip of the needle 50 inserted into the collection container 53, and simultaneously, an amount of gas is ejected from the surrounding gas-introducing tube 50B. By this stream of gas from the gas-introducing tube 50B, the solution being dropped from the solution-introducing tube 50A is sheared into fine droplets (mist) and attached to the inner wall of the collection container 53. Since the collection container 53 is preheated by the temperature regulation block 54 surrounding the container, the solvent in the fine droplets which have attached to the inner wall vaporizes, leaving only the target component (solute) in the form of powder. The gas introduced into the collection container 53 and the vaporized solvent are discharged from the gap between the hole and the needle 50, through the exhaust duct 55 to the outside of the collection container 53.

BACKGROUND ART DOCUMENT

Patent Document

Patent Document 1: JP-A 2003-149217
Patent Document 2: WO 2009/044425
Patent Document 3: WO 2009/044426
Patent Document 4: WO 2009/044427
Patent Document 5: WO 2009/044428

SUMMARY OF THE INVENTION

Problem to be Solved by the Invention

In the gas-blowing vaporizing and drying process shown in FIGS. 8A-8D, the obtained powder of the target compound is scattered within the collection container 53 by the gas ejected from the gas-introducing tube 50B. A portion of the scattered powder attaches to the outer surface of the needle 50 during the process, which will cause carry-over contamination when the powdering of a different component is performed in the next collection container.

To prevent such contamination, the preparative separation-purification system is provided with a port for washing the tip of the needle. Every time the preparation of the powder of one component is completed in one collection container, the needle is moved to the port and its tip is washed. However, if there are a large number of components to be consecutively subjected to the powdering process, washing the needle for every completion of the powdering of one component requires a considerable amount of time for the washing.

The present invention has been developed to solve the aforementioned problem, and its objective is to provide a gas-blowing vaporizing and drying device which does not cause contamination by the powder scattered in the gas-blowing vaporizing and drying process.

Means for Solving the Problems

A gas-blowing vaporizing and drying device according to the present invention aimed at solving the previously described problem includes:

a sample tube in the form of a double tube including an inner tube for a solution and an outer tube for a gas, the inner tube protruding from one end of the outer tube by length L; and a collection container including a container body and a lid provided with a protrusion sleeve tube, the protrusion sleeve tube including a coupling portion at an end to be located outside the container body and a sleeve portion of a length equal to or longer than L having an open end to be located inside the container body, the coupling portion being designed to be coupled to the aforementioned one end of the outer tube in an air-tight manner.

In the gas-blowing vaporizing and drying device according to the present invention, a solution and a gas are supplied under the condition that the outer tube of the sample tube is coupled to the coupling portion of the protrusion sleeve tube provided in the lid of the collection container, with the protruding section of the inner tube of the sample tube inserted into the sleeve portion of the protrusion sleeve tube. This coupling creates a double-tube structure with the protruding section of the inner tube of the sample tube functioning as the inner tube and the sleeve portion of the protrusion sleeve tube functioning as the outer tube, thus allowing the solution and the gas to pass through the inner and outer tubes, respectively. With this double-tube structure of the protruding section of the inner tube of the sample tube and the sleeve portion, the gas-blowing vaporizing and drying device according to the present invention can perform the previously described gas-blowing vaporizing and drying process. Furthermore, in the gas-blowing vaporizing and drying device according to the present invention, both the inner and outer tubes of the sample tube are prevented from being contaminated by the powder scattered in the process, since the outer tube of the sample tube is not inserted into the container body while the protruding section (length L) of the inner tube of the sample tube is shielded by the sleeve portion of the protrusion sleeve tube with a length equal to or longer than L. Therefore, the aforementioned contamination will not occur when the powdering of a different kind of component is performed in the next collection container.

In the gas-blowing vaporizing and drying device according to the present invention, the nebulizing efficiency of the solution depends on the inner shape of the protrusion sleeve tube (particularly, the sleeve portion) as well as the position of the tip of the protrusion sleeve tube relative to the tip of the solution tube (i.e. the inner tube of the sample tube). To improve the solution-nebulizing efficiency, the protrusion sleeve tube and the sample tube may preferably be designed in such a manner that the sleeve portion of the protrusion sleeve tube has a narrow portion whose inner cross-sectional area is smaller than that of the other portion and the aforementioned length L is determined so that the tip of the inner tube is located at the narrow portion when the aforementioned one end of the outer tube is coupled to the coupling portion of the protrusion sleeve tube. By this design, the gas stream passing through the protrusion sleeve tube is concentrated into the vicinity of the tip of the inner tube, thus helping the shearing of the solution dropped from the solution tube.

A tubular cover having an inner space whose cross-sectional area gradually increases toward the distal end may preferably be attached to the aforementioned open end of the protrusion sleeve tube. This cover prevents the mist ejected from the aforementioned open end from being dispersed over the entire inner wall of the container body, and the largest portion of the mist attaches to the inner wall in the areas lower than the cover and turns into powder. Accordingly, the powdered target component can be more easily scraped off the inner wall surface.

Effect of the Invention

As compared to the conventional gas-blowing vaporizing and drying device, the gas-blowing vaporizing and drying device according to the present invention is characterized in that each collection container has the protrusion sleeve tube provided in the lid. This protrusion sleeve tube prevents the sample tube consisting of the inner tube for a solution and the outer tube for a gas from being contaminated by the powder scattered in the process. Therefore, no contamination occurs even if the powdering of different kinds of solutes is continuously performed. The gas-blowing vaporizing and drying device according to the present invention can be suitably used in a preparative separation-purification system.

BRIEF DESCRIPTION OF THE DRAWINGS

FIG. 1 is a schematic configuration diagram of a preparative separation-purification system using a gas-blowing vaporizing and drying device according to one embodiment of the present invention.

FIG. 2A is a schematic vertical sectional view of a collection container and a sample tube in the gas-blowing vaporizing and drying device of the present embodiment, and FIG. 2B is a schematic vertical sectional view of the same device with the outer tube of the sample tube coupled to the protrusion sleeve tube provided in the collection container.

FIG. 3A is a diagram showing the dimensions of the parts around the tip of the sleeve portion of the protrusion sleeve tube when the outer tube of the sample tube is coupled to the protrusion sleeve tube, and FIG. 3B is a photograph showing the state of the powder obtained in a collection container by using the sample tube and the protrusion sleeve tube with the dimensions as shown in FIG. 3A.

FIG. 4A is a schematic configuration diagram showing the position relationship of the protrusion sleeve tube and the inner tube of the sample tube when the outer tube of the sample tube is coupled to the protrusion sleeve tube so that the tips of the inner tube and the protrusion sleeve tube are located at the same level, and FIG. 4B is a photograph showing the state of the powder obtained in a collection container under that condition.

FIG. 5A is a schematic configuration diagram showing the position relationship of the protrusion sleeve tube and the inner tube of the sample tube when the outer tube of the sample tube is coupled to the protrusion sleeve tube so that the inner tube of the sample tube protrudes from the protrusion sleeve tube, and FIG. 5B is a photograph showing the state of the powder obtained in a collection container under that condition.

FIG. 6A is a schematic diagram showing a modification example of the protrusion sleeve tube used in the gas-blowing vaporizing and drying device of the present embodiment, and FIG. 6B is a schematic diagram showing the same device with the sample tube connected to the protrusion sleeve tube of this modification example.

FIG. 7 is a photograph showing the state of the powder obtained in a collection container by using the gas-blowing vaporizing and drying device of the modification example.

FIGS. 8A-8D are diagrams illustrating the powdering process by a conventional preparative separation-purification system.

BEST MODE FOR CARRYING OUT THE INVENTION

A preparative separation-purification system using a gas-blowing vaporizing and drying device according to one embodiment of the present invention is hereinafter described with reference to the schematic configuration diagram shown in FIG. 1. As will be described later, this preparative separation-purification system is designed to process a solution containing a target component which is fractionated beforehand by a preparative liquid chromatograph (not shown). It is also possible to change the configuration by directly connecting the preparative liquid chromatograph to the preparative separation-purification system so that a solution fractionated by the preparative liquid chromatograph is directly introduced into the preparative separation-purification system.

Figure 1:
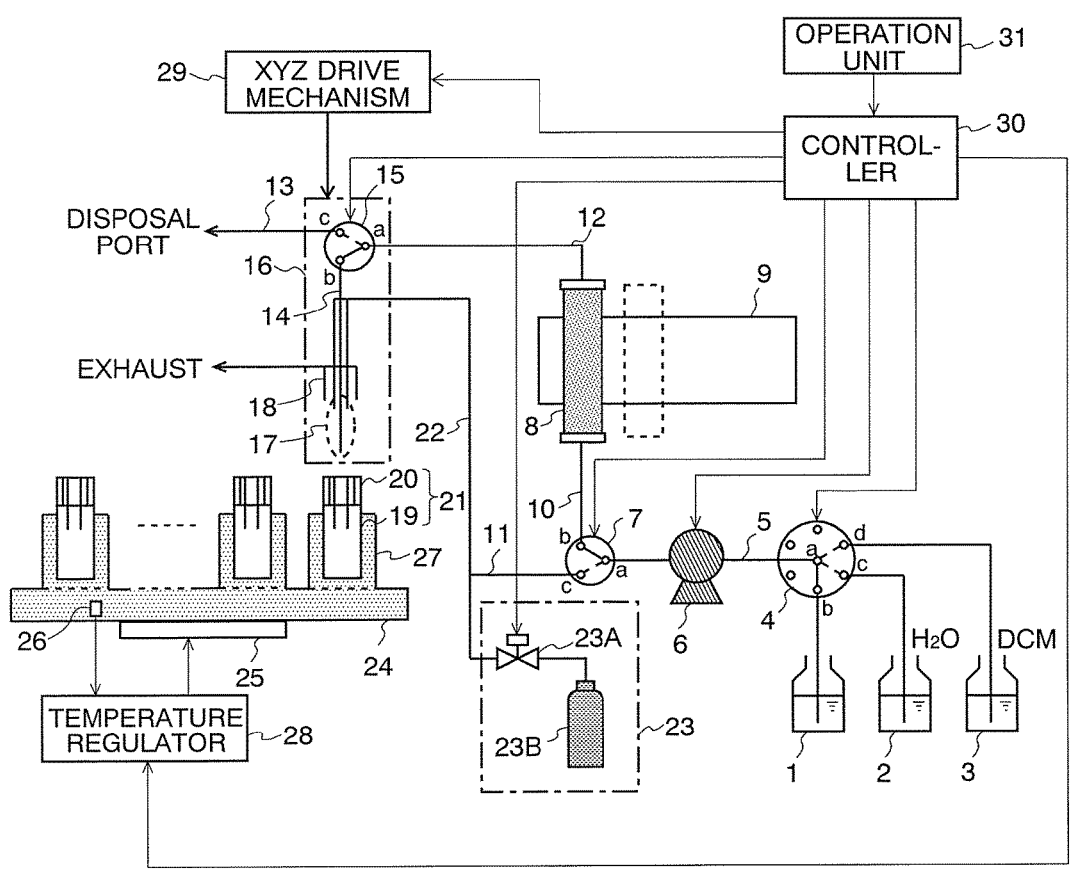

In FIG. 1, a solution container 1 holds a previously fractionated solution containing a target component. The solvent of this solution is mainly the mobile phase used in the preparative liquid chromatograph. A pure water container 2 holds pure water ($H_2O$), while an eluting solvent container 3 holds dichloromethane (DCM). A selector valve 4 switches the passage so as to selectively allow one of the three kinds of liquid held in the containers 1, 2 and 3 to flow into a passage 5. A liquid-sending pump 6 for drawing and sending the liquid at a predetermined flow rate is provided in the passage 5.

The outlet end of the passage 5 is connected to port a of a selector valve 7. A passage 10 leading to a trap column 8 packed with an adsorbent for capturing the target component is connected to port b of the selector valve 7, and a passage 11 leading to a gas passage 22 (which will be described later) is connected to port c. The selector valve 7 selectively connects either the passage 10 or 11 to the passage 5.

The trap column 8 is held in a substantially vertical position by a column rack 9, with the inlet end (to which the passage 10 is to be connected) directed downward and the outlet end (to which a passage 12 is to be connected, as will be described later) directed upward. Although only one trap column 8 is shown in FIG. 1, the column rack 9 can hold a plurality of trap columns 8, as indicated by the dotted line in FIG. 1.

The passage 12, with one end connected to the outlet end of the trap column 8, has the other end connected to port a of a selector valve 15, which is incorporated in a fraction collector head 16. A passage 14 is connected to port b of the selector valve 15, and a passage 13 leading to a disposal port is connected to port c. The selector valve 15 selectively connects either the passage 13 or 14 to the passage 12.

Figure 2A:
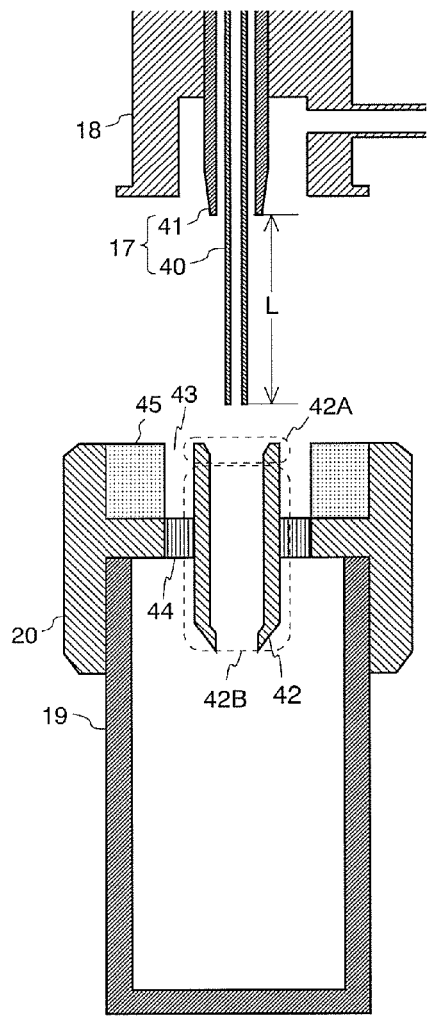

The fraction collector head 16, which is provided with a sample tube 17 and an exhaust duct 18, can be moved in both vertical and horizontal directions by an XYZ drive mechanism 29 composed of a plurality of motors and other components. The sample tube 17 is a double tube having an inner tube 40 connected to the passage 14 and an outer tube 41 connected to the passage 22 (FIG. 2A). As will be described later, a solution containing a target component is supplied through the passage 14 into the inner tube 40, while a gas or dichloromethane is supplied through the passage 22 into the outer tube 41. As a characteristic structure of the present invention, the inner tube 40 of the sample tube 17 protrudes from the lower end of the outer tube 41 by length L.

Each collection container 21, which is used for collecting the target component obtained by the preparative separation and purification process, is individually contained in one of the temperature regulation blocks 27 on a container rack 24, which is provided with a heater 25 and a temperature sensor 26 (e.g. thermistor). The container rack 24 and the temperature regulation blocks 27 are made of a material with high thermal conductivity, such as aluminum. Their outer surfaces are covered with an insulating material to prevent heat from escaping to the surroundings.

Each collection container 21 has at least its bottom portion closely attached to the temperature regulation block 27 so as to facilitate the conduction of heat from the temperature regulation block 27. As a more preferable form, the circumferential side surface of the collection container 21 may also be in contact with the temperature regulation block 27. A temperature regulator 28, which is provided apart from the container rack 24, regulates an electric current supplied to the heater 25 so that the temperature monitored by the temperature sensor 26 will be a target temperature. By this operation, the collection containers 21 are heated to and maintained at an appropriate constant temperature.

Figure 2B:
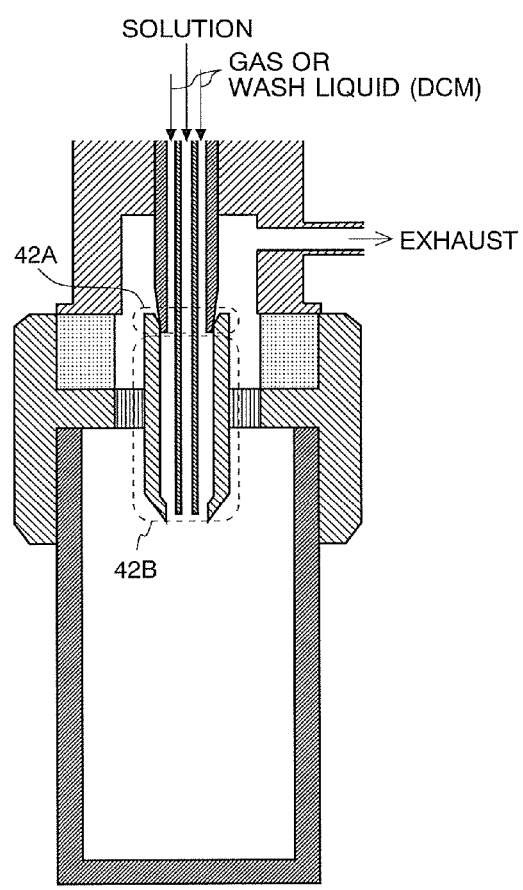

The collection container 21 has a container body 19, with a cap 20 attached on its upper opening. As a characteristic structure of the present invention, the cap 20 has a protrusion sleeve tube 42 (which is hereinafter simply called the "sleeve tube") and an exhaust port 43 (FIG. 2A). The sleeve tube 42 has a coupling portion 42A at its inlet end to be coupled to the tip of the outer tube 41 of the sample tube 17 in an air-tight manner, and a sleeve portion 42B at its outlet end for covering the protruding portion of the inner tube 40 of the sample tube 17 (FIG. 2B). The sleeve portion 42B has a length equal to or longer than the length L of the protruding portion of the inner tube 40 so that it can entirely cover the protruding portion of the inner tube 40. A filter 44 for preventing the passage of a powdered solute is provided in the exhaust port 43. The cap 20 is further provided with a doughnut-shaped cushion 45 for enhancing the seal between the cap 20 and the exhaust duct 18.

The fraction collector head 16 is moved by the XYZ drive mechanism 29 to a position above any one of the collection containers 21 held in the container rack 24, and then lowered. By this operation, as shown in FIG. 2B, the protruding portion of the inner tube 40 of the sample tube 17 is inserted into the sleeve portion 42B, and the outer tube 41 of the sample tube 17 is coupled with the coupling portion 42A. As already described, the sleeve section 42B is longer than the length L of the protruding portion of the inner tube 40. Accordingly, the protruding portion of the inner tube 40 of the sample tube 17 is entirely covered with the sleeve portion 42B. Along with the descending motion of the sample tube 17, the exhaust duct 18 is also moved downward, being hermetically pressed on the cap 20 by an elastic force of the cushion 45 provided in the cap 20. In this state, the gas-blowing vaporizing and drying process is performed, as will be described later.

Instead of the XYZ drive mechanism 29 for moving the fraction collector head 16, a drive mechanism for moving the container rack 24 may be used for the coupling of the outer tube 41 to the coupling portion 42A.

The gas supply unit 23, which includes a proportional valve 23A, a gas cylinder 23B and other components, supplies gas through the passage 22 into the outer tube 41 of the sample tube 17.

The controller 30, which includes a central processing unit (CPU) and other components, automatically conducts the preparative separation-purification process by controlling the switching operations of the selector valves 4, 7 and 15, the operations (flow rate or flow velocity) of the liquid-sending pump 6 and the gas supply unit 23, the setting of the target temperature of the temperature regulator 28, the motion of the fraction collector head 16 through the XYZ drive mechanism 29 and other operations according to a predetermine program. An operation unit 31 is provided to allow users to enter and set the conditions for the preparative separation-purification process as well as other information.

A procedure of the gas-blowing vaporizing and drying process performed by the preparative separation-purification system of FIG. 1 is hereinafter described. Initially, the controller 30 sets the selector valves 4, 7 and 15 to create a passage for capturing a target component on the adsorbent in the trap column 8. Specifically, the selector valve 4 is set to connect the solution container 1 (port b) and the passage 5 (port a), the selector valve 7 is set to connect the passage 5 (port a) and the passage 10 (port b), and the selector valve 15 is set to connect the passages 12 and 13. Subsequently, the liquid-sending pump 6 is energized to supply liquid at a predetermined flow rate.

The liquid-sending pump 6 draws the solution from the solution container 1 and sends it into the trap column 8. While the solution is passing through the trap column 8, the target component in the solution is captured on the adsorbent in the trap column 8. The mobile phase from which the target component has been removed is discharged through the passages 12 and 13 into the disposal port.

After the solution is supplied to the trap column 8 for a predetermined period of time or until the solution prepared in the solution container 1 is completely used, the controller 30 switches the selector valve 4 so as to connect the pure water container 2 (port c) and the passage 5 (port a). Then, the liquid-sending pump 6 begins to draw pure water from the pure water container 2 and send it into the trap column 8. As a result, unwanted water-soluble substances, such as salt that has adhered to the adsorbent during the preceding process of capturing the target component, are removed from the trap column 8. By this supply of pure water, the mobile phase remaining inside the trap column 8 immediately before the beginning of the supply of water is replaced by the water, and the trap column 8 becomes filled with water. The target component captured on the adsorbent is strongly adsorbed and barely eluted into the water. Therefore, at this point, the target component remains in the captured state within the trap column 8.

Subsequently, the controller 30 moves the fraction collector head 16 by the XYZ drive mechanism 29 to a position above a previously designated collection container 21, and lowers the fraction collector head 16 so as to couple the tip of the outer tube 41 of the sample tube 17 to the coupling portion 42A of the sleeve tube 42 (FIG. 2B). As a result, the protruding portion of the inner tube 40 of the sample tube 17 is inserted into the sleeve tube 42. The exhaust duct 18 is also moved downward, being hermetically pressed on the cap 20 by an elastic force of the cushion 45 provided in the cap 20. After that, the selector valve 4 is switched so as to connect the eluting solvent container 3 (port d) and the passage 5 (port a). Then, the liquid-sending pump 6 begins to draw dichloromethane from the eluting solvent container 3 and send it into the trap column 8. In this process, the liquid-sending pump 6 is operated at a predetermined liquid-sending flow rate lower than in the previously described operation of sending the solution or pure water. The controller 30 also orders the temperature regulator 28 to begin the heating of the temperature regulation block 27, giving an instruction on the target temperature. Thus, the collection container 21 begins to be heated. The target temperature is, for example, set to be approximately equal to or slightly higher than the boiling point of dichloromethane, e.g. from 40 to 45 degrees Celsius.

The dichloromethane introduced into the trap column 8 becomes barely mixed with the water in the trap column 8, and the interface between the dichloromethane and the water gradually ascends. That is to say, the dichloromethane level gradually rises from the bottom of the trap column 8, pushing the water upward. The water thus pushed overflows from the upper outlet end of the trap column 8 and flows through the selector valve 15 and the passage 13 to the disposal port. Meanwhile, due to the strong eluting power of the dichloromethane, the target component captured in the trap column 8 is eluted into the dichloromethane being accumulated in the trap column 8.

After a predetermined period of time, when the water is completely removed from the trap column 8, the selector valve 15 is switched from the passage 13 (port c) to the passage 14 (port b) to initiate the preparative separation of the target component. Furthermore, the controller 30 orders the gas supplier 23 to begin the supply of nitrogen gas (or another inert gas). The gas supplied from the gas supplier 23 flows through the passage 22 and the outer tube 41 into the sleeve tube 42, and begins to be emitted from the tip of the sleeve portion 42B. The solution coming from the trap column 8, i.e. the dichloromethane containing the target component, flows through the passages 12 and 14, to be eventually dropped from the tip of the inner tube 40 of the sample tube 17 whose protruding portion is inserted in the sleeve tube 42. While being dropped, the solution is sheared into fine droplets and scattered around by the gas stream blowing around them. To improve the shearing (nebulizing) efficiency of the solution, the sleeve tube 42 in the present embodiment is designed so that its inner diameter is smaller at a tip section of the sleeve portion 42B and the length of the sleeve portion 42B is adjusted so that the tip of the inner tube 40 is located at that tip section (the section with the smaller diameter). By this design, the gas stream passing through the sleeve tube 42 is concentrated in the vicinity of the tip of the inner tube 40, thus helping the shearing of the solution dropped from the inner tube 40.

The collection container 21 is heated to a temperature as high as the boiling point of dichloromethane by heat conduction from the temperature regulation block 27 with the heater 25 as the heat source. Therefore, when the fine droplets of the solution attach to the inner circumferential wall or the inner bottom wall of the collection container 21, the solvent (dichloromethane) in the droplets immediately vaporizes, leaving the target component in the powder form. The resulting powder of the target component collects on the inner circumferential wall and the inner bottom wall of the collection container 21. The gas introduced into the collection container 21 and the vaporized solvent are discharged through the exhaust port 43 and the exhaust duct 18 to the outside of the collection container 21.

After the previously described processes are completed, the fraction collector head 16 is moved upward. If the powdering process for another target component is to be subsequently performed, the fraction collector head 16 is moved to the position where the next collection container 21 is set, and the processes are similarly performed.

While the gas-blowing vaporizing and drying process of the present embodiment using the preparative separation-purification system of FIG. 1 is performed in the previously described manner, the solute may possibly deposit on the tip of the inner tube 40 of the sample tube 17 and clog the gas ejection port between the inner tube 40 and the sleeve tube 42. In such a case, the gas supply from the gas supply unit 23 is temporarily discontinued, and the selector valve 7 is switched from the passage 10 (port b) to the passage 11 (port c). The dichloromethane drawn from the eluting solvent container 3 is now redirected to the passage 11, and the dropping of the solution from the trap column 8 into the collection container 21 stops.

The dichloromethane sent to the passage 11 is introduced into the passage 22, and flows through the outer tube 41 into the sleeve tube 42. As already noted, dichloromethane has a strong eluting power. Therefore, the deposited solute clogging the gas ejection port of the sleeve tube 42 is dissolved in the introduced dichloromethane and washed away. Subsequently, the selector valve 7 is switched from the passage 11 (port c) to the passage 10 (port b) and the gas supply from the gas supply unit 23 is resumed, whereby the previously described gas-blowing vaporizing and drying process is continued.

Figure 3A:
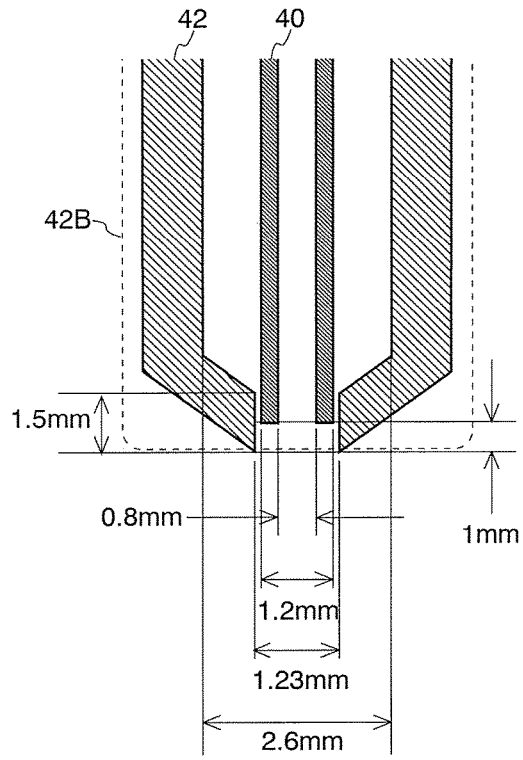
Figure 3B:
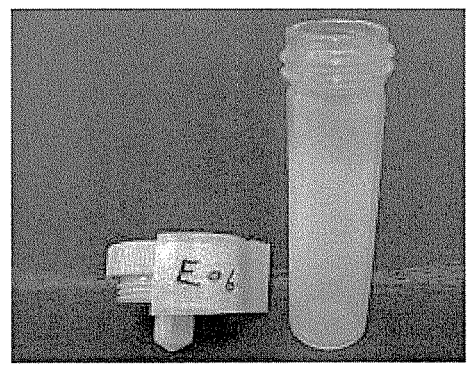
Figure 4A:
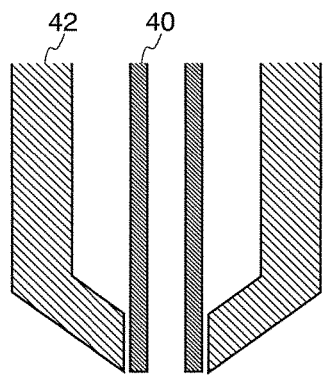
Figure 4B:
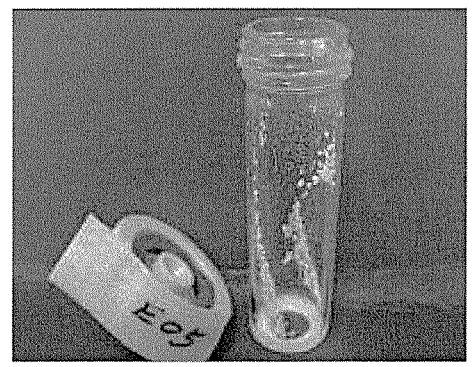
Figure 5A:
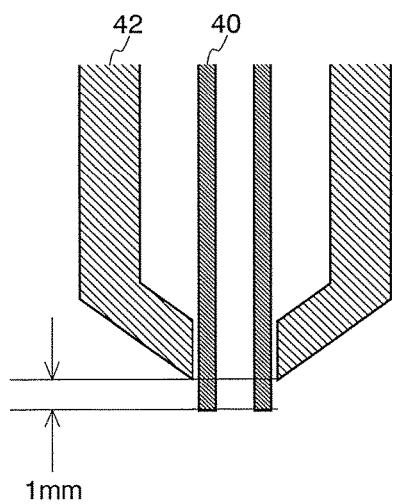
Figure 5B:

The powdering performance of the gas-blowing vaporizing and drying device of the present embodiment depends on the position of the tip of the inner tube 40 of the sample tube 17 relative to the tip of the sleeve tube 42 when the outer tube 41 of the sample tube 17 is coupled to the coupling portion 42A of the sleeve tube 42. To confirm this fact, three experiments have been performed using different setups of the device. FIG. 3A shows the setup for the first experiment, in which the inner diameter of the inner tube 40 was 0.8 mm, its outer diameter was 1.2 mm, the inner diameter of the sleeve tube 42 at the tip section (with a length of 1.5 mm from the tip) was 1.23 mm, the inner diameter of the sleeve portion 42B at the other section was 2.6 mm, and the protruding portion of the inner tube 40 was 1 mm shorter than the sleeve portion 42B of the sleeve tube 42. In this experiment, the state of the powder obtained in the container body 19 was as shown in the photograph of FIG. 3B. In the second experiment, the protruding portion of the inner tube 40 had the same length as the sleeve portion 42B of the sleeve tube 42 (FIG. 4A). The state of the powder obtained in the container body 19 was as shown in the photograph of FIG. 4B. The third experiment was performed as a comparative example, with the protruding portion of the inner tube 40 1 mm longer than the sleeve portion 42B of the sleeve tube 42 (FIG. 5A). The state of the powder obtained in the container body 19 was as shown in the photograph of FIG. 5B. In any of these experiments, the flow rate of the solution introduced into the inner tube 40 was 0.1 mL/min (it should be noted that the flow rate was variable within a range from 0.1 to 0.5 mL/min depending on the method used), and the flow rate of the gas introduced into the outer tube 41 was 1.6 L/min. Both the inner tube 40 and the sleeve tube 42 were made of PEEK (polyetheretherketone) resin. The outer tube 41 was made of SUS (steel use stainless).

In the photograph of FIG. 3B, the powder is found on the entirety of the inner wall surface of the container body 19, with almost no solution remaining inside. By contrast, in the photograph of FIG. 4B, the powder can be found only on a portion of the inner wall surface. Furthermore, an oily deposit of the solution which did not turn into powder can be found at the bottom of the container body 19. In the photograph of FIG. 5B, almost no powder can be found on the inner wall surface, while the amount of oily solution deposited at the bottom of the container body 19 is the largest.

These results suggest that the length of the protruding portion of the inner tube 40 and that of the sleeve portion 42B of the sleeve tube 42 should preferably be designed so that the tip of the inner tube 40 is located behind the tip of the sleeve tube 42. Furthermore, the tip of the inner tube 40 should preferably be located at the portion of the sleeve tube 42 having the smaller inner diameter.

FIG. 6A shows a modification of the sleeve tube 42. In this modification, a tubular cover 46 having an inner space whose cross-sectional area gradually increases toward the distal end is attached to the tip of the sleeve tube 42. This cover 46 may be removable from and attachable to the sleeve tube 42, or it may be integrated with the sleeve tube 42 as a single part. When this cover 46 is provided, the powder will mainly attach to the lower portion of the inner wall surface of the container body 19, as shown in the photograph of FIG. 7. Accordingly, the powdered target component can be more easily scraped off the inner wall surface.

Thus far, the gas-blowing vaporizing and drying device according to the present invention has been described by means of the embodiment. Naturally, the embodiment can be appropriately changed or modified within the spirit of the present invention.

EXPLANATION OF NUMERALS

1 . . . Solution Container
2 . . . Pure Water Container
3 . . . Eluting Solvent Container
4 . . . Selector Valve
5, 10, 11, 12, 13, 14, 22 . . . Passage
6 . . . Liquid-Sending Pump
7 . . . Selector Valve
8 . . . Trap Column
9 . . . Column Rack
15 . . . Selector Valve
16 . . . Fraction Collector Head
17 . . . Sample Tube
40 . . . Inner Tube
41 . . . Outer Tube
18 . . . Exhaust Duct
19 . . . Container Body
20 . . . Cap
42 . . . Sleeve Tube
42A . . . Coupling Portion
42B . . . Sleeve Portion
43 . . . Exhaust Port
44 . . . Filter
45 . . . Cushion
46 . . . Cover
21 . . . Collection Container
23 . . . Gas Supply Unit
23A . . . Proportional Valve
23B . . . Gas Cylinder
24 . . . Container Rack
25 . . . Heater
26 . . . Temperature Sensor
27 . . . Temperature Regulation Block
28 . . . Temperature Regulator
29 . . . XYZ Drive Mechanism
30 . . . Controller
31 . . . Operation Unit

The invention claimed is:
1. A gas-blowing vaporizing and drying device for nebulizing a solution containing a target component by blowing an amount of gas at the solution being dropped and then drying the solvent to collect the target component in solid form, comprising:

a sample tube in a form of a double tube including an inner tube for the solution and an outer tube for the gas, the inner tube protruding from one end of the outer tube by length L; and a collection container including a container body and a lid provided with a protrusion sleeve tube, the protrusion sleeve tube including a coupling portion at an end to be located outside the container body and a sleeve portion of a length equal to or longer than L having an open end to be located inside the container body, the coupling portion being designed to be coupled to the aforementioned one end of the outer tube in an air-tight manner, wherein, when the coupling portion is coupled to the aforementioned one end of the outer tube of the double tube, while the protrusion with length L of the double tube functions as the inner tube, the protrusion sleeve tube functions to extend the outer tube of the double tube such that the solution and the gas pass through, respectively, the inner tube and outer tube extended by the protrusion sleeve tube.

2. The gas-blowing vaporizing and drying device according to claim 1, wherein the sleeve portion of the protrusion sleeve tube has a narrow portion whose inner cross-sectional area is smaller than that of another portion, and the aforementioned length L is determined so that the tip of the inner tube is located at the narrow portion when the aforementioned one end of the outer tube is coupled to the coupling portion of the protrusion sleeve tube.

3. The gas-blowing vaporizing and drying device according to claim 1, wherein a tubular cover having an inner space whose cross-sectional area gradually increases toward a distal end is attached to the aforementioned open end of the protrusion sleeve tube.

4. The gas-blowing vaporizing and drying device according to claim 2, wherein a tubular cover having an inner space whose cross-sectional area gradually increases toward a distal end is attached to the aforementioned open end of the protrusion sleeve tube.

5. A gas-blowing vaporizing and drying device for nebulizing a solution containing a target component by blowing an amount of gas at the solution being dropped and then drying the solvent to collect the target component in solid form, the gas-blowing vaporizing and drying device comprising:

a lid provided with a protrusion sleeve tube, the protrusion sleeve tube including a coupling portion at an end and a sleeve portion of a length equal to or longer than L, and a sample tube in a form of a double tube including an inner tube for the solution and an outer tube for the gas being designed to be coupled to the coupling portion in an air-tight manner, with the inner tube protruding from one end of the outer tube by length L, wherein, when the coupling portion is coupled to the aforementioned one end of the outer tube of the double tube, while the protrusion with length L of the double tube functions as the inner tube, the protrusion sleeve tube functions to extend the outer tube of the double tube such that the solution and the gas pass through, respectively, the inner tube and outer tube extended by the protrusion sleeve tube.

* * * * *